(12) United States Patent
Dubois et al.

(10) Patent No.: US 8,815,099 B1
(45) Date of Patent: Aug. 26, 2014

(54) DEVICES AND METHODS FOR FILTERING AND/OR COLLECTING TISSUE

(71) Applicant: Laurimed, LLC, Redwood City, CA (US)

(72) Inventors: Brian R. Dubois, Redwood City, CA (US); James T. Nielsen, San Francisco, CA (US); Alexander Gordon, Menlo Park, CA (US)

(73) Assignee: Laurimed, LLC, Redwood City, CA (US)

( * ) Notice: Subject to any disclaimer, the term of this patent is extended or adjusted under 35 U.S.C. 154(b) by 0 days.

(21) Appl. No.: 14/160,095

(22) Filed: Jan. 21, 2014

(51) Int. Cl.
*B01D 37/00* (2006.01)
*B01D 35/02* (2006.01)
*B01D 29/11* (2006.01)
*A61M 1/00* (2006.01)

(52) U.S. Cl.
CPC .................................. *A61M 1/0056* (2013.01)
USPC ........ 210/767; 210/416.1; 210/455; 210/457; 210/787; 210/488; 604/190; 604/406

(58) Field of Classification Search
CPC .............. A61B 10/00; A61B 10/0096; A61M 2202/09; A61M 1/0056; A61M 2525/003; A61M 2202/005; A61M 2205/75; B01D 29/00; A01B 12/006
USPC ............... 210/767, 808, 416.1, 455, 457, 487
See application file for complete search history.

(56) References Cited

U.S. PATENT DOCUMENTS

| | | | |
|---|---|---|---|
| 1,527,291 A | 2/1925 | Zorraquin | |
| 1,733,502 A | 10/1929 | Linsley | |
| 2,895,455 A | 7/1959 | Clowes | |
| 3,081,770 A | 3/1963 | Hunter | |
| 3,401,684 A | 9/1968 | Dremann | |
| 3,469,580 A | 9/1969 | Huddy | |
| 3,561,429 A | 2/1971 | Jewett et al. | |
| 3,682,162 A | 8/1972 | Colyer | |
| 3,689,955 A | 9/1972 | Winkelmann | |
| 3,709,211 A | 1/1973 | Hawkins | |
| 3,782,381 A | 1/1974 | Winnie | |
| 3,809,093 A | 5/1974 | Abraham | |
| 3,815,604 A | 6/1974 | O'Malley et al. | |
| 3,884,238 A | 5/1975 | O'Malley et al. | |
| 3,941,127 A | 3/1976 | Froning | |
| 3,943,932 A | 3/1976 | Woo | |
| 3,977,400 A | 8/1976 | Moorehead | |
| 4,013,080 A | 3/1977 | Froning | |
| 4,068,659 A | 1/1978 | Moorehead | |
| 4,192,319 A | 3/1980 | Hargens et al. | |
| 4,314,560 A | 2/1982 | Helfgott et al. | |
| RE30,966 E | 6/1982 | Hargens et al. | |
| 4,349,023 A | 9/1982 | Gross | |
| 4,368,730 A | 1/1983 | Sharrock | |
| 4,428,748 A | 1/1984 | Peyman et al. | |
| 4,434,053 A * | 2/1984 | Osuna-Diaz | 210/446 |
| 4,507,167 A | 3/1985 | Jahme et al. | |
| 4,511,356 A | 4/1985 | Froning et al. | |
| 4,580,573 A | 4/1986 | Quinn | |
| 4,588,399 A | 5/1986 | Nebergall et al. | |
| 4,609,370 A | 9/1986 | Morrison | |
| 4,662,869 A | 5/1987 | Wright | |
| 4,678,459 A | 7/1987 | Onik et al. | |
| 4,721,506 A | 1/1988 | Teves | |
| 4,737,146 A | 4/1988 | Amaki et al. | |
| 4,775,637 A | 10/1988 | Sutherland et al. | |
| 4,808,157 A | 2/1989 | Coombs | |
| 4,842,585 A | 6/1989 | Witt | |
| 4,846,799 A | 7/1989 | Tanaka et al. | |
| 4,886,067 A | 12/1989 | Palermo | |
| 4,886,492 A | 12/1989 | Brooke | |
| 4,917,668 A | 4/1990 | Haindl | |
| 4,917,670 A | 4/1990 | Hurley et al. | |
| RE33,258 E | 7/1990 | Onik et al. | |
| 4,940,458 A | 7/1990 | Cohn | |
| 4,958,901 A | 9/1990 | Coombs | |
| 4,973,305 A | 11/1990 | Goltzer | |
| 4,973,312 A | 11/1990 | Andrew | |
| 4,994,036 A | 2/1991 | Biscoping et al. | |
| 5,004,456 A | 4/1991 | Botterbusch et al. | |
| 5,007,902 A | 4/1991 | Witt | |
| 5,024,655 A | 6/1991 | Freeman et al. | |
| 5,026,350 A | 6/1991 | Tanaka et al. | |
| 5,060,658 A | 10/1991 | Dejter, Jr. et al. | |

(Continued)

FOREIGN PATENT DOCUMENTS

| | | |
|---|---|---|
| EP | 0746245 | 11/2002 |
| GB | 529 800 | 11/1940 |

(Continued)

OTHER PUBLICATIONS

Sice et al. "Epidural analgesia after spinal surgery via intervertebral foramen," *British Journal of Anaesthesia*, 94(3), pp. 378-380, Dec. 24, 2004.

*Primary Examiner* — Nam Nguyen
*Assistant Examiner* — Claire Norris
(74) *Attorney, Agent, or Firm* — Levine Bagade Han LLP

(57) ABSTRACT

Various devices and methods for filtering and/or collecting tissue which has been cut or resected from various regions of a patient's body are described herein. In certain variations, a filter or tissue collection chamber may include various components, which allow for the removal or separation of tissue from a fluid medium and for the collection of the tissue within the filter or tissue collection chamber.

25 Claims, 6 Drawing Sheets

(56) References Cited

U.S. PATENT DOCUMENTS

| | | | |
|---|---|---|---|
| 5,078,679 A | 1/1992 | Reese | |
| 5,085,631 A | 2/1992 | Leighton | |
| 5,085,659 A | 2/1992 | Rydell | |
| 5,098,388 A | 3/1992 | Kulkashi et al. | |
| 5,100,379 A | 3/1992 | Wendell | |
| 5,100,390 A | 3/1992 | Lubeck et al. | |
| 5,106,376 A | 4/1992 | Mononen et al. | |
| 5,119,832 A | 6/1992 | Xavier | |
| 5,129,889 A | 7/1992 | Hahn et al. | |
| 5,135,525 A | 8/1992 | Biscoping et al. | |
| 5,152,744 A | 10/1992 | Krause et al. | |
| 5,160,323 A | 11/1992 | Andrew | |
| 5,163,901 A | 11/1992 | Eldor | |
| 5,176,628 A | 1/1993 | Charles et al. | |
| 5,205,828 A | 4/1993 | Kedem | |
| 5,207,647 A | 5/1993 | Phelps | |
| 5,209,734 A | 5/1993 | Hurley et al. | |
| 5,213,578 A | 5/1993 | Heiliger et al. | |
| 5,232,442 A | 8/1993 | Johnson et al. | |
| 5,234,406 A | 8/1993 | Drasner et al. | |
| 5,257,972 A | 11/1993 | Gurmarnik | |
| 5,263,936 A | 11/1993 | Yurino | |
| 5,269,769 A | 12/1993 | Dhara et al. | |
| 5,292,310 A | 3/1994 | Yoon | |
| 5,304,141 A | 4/1994 | Johnson et al. | |
| 5,306,239 A | 4/1994 | Gurmarnik et al. | |
| 5,312,374 A | 5/1994 | Gurmarnik | |
| 5,312,375 A | 5/1994 | Gurmarnik | |
| 5,320,610 A | 6/1994 | Yoon | |
| 5,328,479 A | 7/1994 | Gurmarnik | |
| 5,335,671 A | 8/1994 | Clement | |
| 5,368,573 A | 11/1994 | Andrew | |
| 5,376,082 A | 12/1994 | Phelps | |
| 5,385,561 A | 1/1995 | Cerny | |
| 5,392,790 A | 2/1995 | Kanner et al. | |
| 5,405,334 A | 4/1995 | Roth et al. | |
| 5,417,208 A | 5/1995 | Winkler | |
| 5,423,760 A | 6/1995 | Yoon | |
| 5,423,770 A | 6/1995 | Yoon | |
| 5,425,717 A | 6/1995 | Mohiuddin | |
| 5,429,596 A | 7/1995 | Arias et al. | |
| 5,449,351 A | 9/1995 | Zohmann | |
| 5,470,318 A | 11/1995 | Griffith, III et al. | |
| 5,480,389 A | 1/1996 | McWha et al. | |
| 5,490,845 A | 2/1996 | Racz | |
| 5,512,045 A | 4/1996 | Gurchumelidze | |
| 5,512,052 A | 4/1996 | Jesch | |
| 5,520,652 A | 5/1996 | Peterson | |
| 5,542,918 A | 8/1996 | Atkinson | |
| 5,569,178 A | 10/1996 | Henley | |
| 5,573,519 A | 11/1996 | Zohmann | |
| 5,584,820 A | 12/1996 | Gurmarnik | |
| 5,591,132 A | 1/1997 | Carrie | |
| 5,611,778 A | 3/1997 | Brinon | |
| 5,628,734 A | 5/1997 | Hatfalvi | |
| 5,630,802 A | 5/1997 | Moellmann et al. | |
| 5,630,939 A | 5/1997 | Bulard et al. | |
| 5,637,096 A | 6/1997 | Yoon | |
| 5,669,394 A | 9/1997 | Bergey et al. | |
| 5,669,876 A | 9/1997 | Schechter et al. | |
| 5,669,882 A | 9/1997 | Pyles | |
| 5,672,158 A | 9/1997 | Okada et al. | |
| 5,685,852 A | 11/1997 | Turkel et al. | |
| 5,725,504 A | 3/1998 | Collins | |
| 5,730,754 A | 3/1998 | Obenchain | |
| 5,752,969 A | 5/1998 | Cunci et al. | |
| 5,779,666 A | 7/1998 | Teirstein | |
| 5,779,680 A | 7/1998 | Yoon | |
| 5,820,588 A | 10/1998 | Howard, III | |
| 5,830,188 A | 11/1998 | Abouleish | |
| 5,833,662 A | 11/1998 | Stevens | |
| 5,836,914 A | 11/1998 | Houghton | |
| 5,836,916 A | 11/1998 | Corn | |
| 5,846,226 A | 12/1998 | Urmey | |
| 5,853,391 A | 12/1998 | Bell | |
| 5,857,996 A | 1/1999 | Snoke | |
| 5,871,470 A | 2/1999 | McWha | |
| 5,885,217 A | 3/1999 | Gisselberg et al. | |
| 5,899,891 A | 5/1999 | Racz | |
| 5,913,857 A | 6/1999 | Ritchart et al. | |
| 5,941,853 A | 8/1999 | Collins | |
| 5,957,881 A | 9/1999 | Peters et al. | |
| 5,976,110 A | 11/1999 | Greengrass et al. | |
| 6,004,293 A | 12/1999 | Bell | |
| 6,039,748 A | 3/2000 | Savage et al. | |
| 6,068,642 A | 5/2000 | Johnson et al. | |
| 6,095,149 A | 8/2000 | Sharkey et al. | |
| 6,113,569 A | 9/2000 | Becker | |
| 6,179,828 B1 | 1/2001 | Mottola et al. | |
| 6,183,254 B1 | 2/2001 | Cohen | |
| 6,190,370 B1 | 2/2001 | Tsui | |
| 6,193,704 B1 | 2/2001 | Winters | |
| 6,221,048 B1 | 4/2001 | Phelps | |
| 6,224,630 B1 | 5/2001 | Bao et al. | |
| 6,245,044 B1 | 6/2001 | Daw et al. | |
| 6,258,111 B1 | 7/2001 | Ross et al. | |
| 6,270,703 B1 * | 8/2001 | Wildman et al. | 264/39 |
| 6,273,873 B1 | 8/2001 | Fleischer | |
| 6,296,624 B1 | 10/2001 | Gerber et al. | |
| 6,298,256 B1 | 10/2001 | Meyer | |
| 6,363,273 B1 | 3/2002 | Mastrorio et al. | |
| 6,371,943 B1 | 4/2002 | Racz et al. | |
| 6,558,353 B2 | 5/2003 | Zohmann | |
| 6,572,593 B1 | 6/2003 | Daum | |
| 6,592,559 B1 | 7/2003 | Pakter et al. | |
| 6,610,066 B2 | 8/2003 | Dinger et al. | |
| 6,620,180 B1 | 9/2003 | Bays et al. | |
| 6,638,238 B1 | 10/2003 | Weber et al. | |
| 6,641,563 B1 | 11/2003 | Vitullo et al. | |
| 6,708,489 B2 | 3/2004 | Massey et al. | |
| 6,709,418 B1 | 3/2004 | Aboul-Hosn et al. | |
| 6,712,773 B1 | 3/2004 | Viola | |
| 6,764,491 B2 | 7/2004 | Frey et al. | |
| 6,872,199 B2 | 3/2005 | Cucin | |
| 6,899,712 B2 | 5/2005 | Moutafis et al. | |
| 6,923,813 B2 | 8/2005 | Phillips et al. | |
| 6,925,333 B2 | 8/2005 | Krebs | |
| 6,979,317 B2 | 12/2005 | Galt et al. | |
| 7,022,109 B1 | 4/2006 | Ditto | |
| 7,120,487 B2 | 10/2006 | Nelson | |
| 7,181,289 B2 | 2/2007 | Pflueger et al. | |
| 7,234,468 B2 | 6/2007 | Johnson et al. | |
| 7,244,263 B2 | 7/2007 | Robison et al. | |
| 7,318,831 B2 | 1/2008 | Alvarez et al. | |
| 7,400,930 B2 | 7/2008 | Sharkey et al. | |
| 7,465,278 B2 | 12/2008 | Cicenas et al. | |
| 7,615,037 B2 * | 11/2009 | Murray et al. | 604/319 |
| 7,632,294 B2 | 12/2009 | Milbodker et al. | |
| 7,647,123 B2 | 1/2010 | Sharkey et al. | |
| 7,727,186 B2 | 6/2010 | Makower et al. | |
| 7,740,631 B2 | 6/2010 | Bleich et al. | |
| 7,806,834 B2 | 10/2010 | Beckman et al. | |
| 7,819,819 B2 | 10/2010 | Quick et al. | |
| 7,828,748 B2 | 11/2010 | Hibner | |
| 7,854,706 B2 | 12/2010 | Hibner | |
| 7,909,822 B2 | 3/2011 | Guerra | |
| 7,918,804 B2 | 4/2011 | Monson et al. | |
| 7,955,057 B2 | 6/2011 | Kuehner et al. | |
| 8,016,846 B2 | 9/2011 | McFarlin et al. | |
| 8,088,119 B2 | 1/2012 | Saal et al. | |
| 8,088,291 B2 * | 1/2012 | Hershberger et al. | 210/767 |
| 8,100,874 B1 | 1/2012 | Jordan | |
| 8,277,393 B2 | 10/2012 | Miller et al. | |
| 8,277,437 B2 | 10/2012 | Saal et al. | |
| 8,292,909 B1 | 10/2012 | DuBois et al. | |
| 8,298,254 B2 | 10/2012 | Dubois et al. | |
| 8,308,746 B2 | 11/2012 | Pravong et al. | |
| 8,366,694 B1 | 2/2013 | Jordan et al. | |
| 8,414,587 B2 | 4/2013 | Saal et al. | |
| 8,657,842 B2 | 2/2014 | DuBois et al. | |
| 2002/0183758 A1 | 12/2002 | Middleton et al. | |
| 2003/0176778 A1 | 9/2003 | Messing et al. | |
| 2003/0212395 A1 | 11/2003 | Woloszko et al. | |
| 2004/0034339 A1 | 2/2004 | Stoller et al. | |

(56) References Cited

U.S. PATENT DOCUMENTS

| | | |
|---|---|---|
| 2004/0049217 A1 | 3/2004 | Ross et al. |
| 2004/0064127 A1 | 4/2004 | Lerner |
| 2004/0092992 A1 | 5/2004 | Adams et al. |
| 2004/0098006 A1 | 5/2004 | Nakanishi |
| 2004/0102760 A1 | 5/2004 | Hsue et al. |
| 2004/0127963 A1 | 7/2004 | Uchida et al. |
| 2004/0210231 A1 | 10/2004 | Boucher et al. |
| 2004/0267282 A1 | 12/2004 | Shkarubo et al. |
| 2005/0004563 A1 | 1/2005 | Racz et al. |
| 2005/0010205 A1 | 1/2005 | Hovda et al. |
| 2005/0090801 A1 | 4/2005 | Racz et al. |
| 2005/0197661 A1 | 9/2005 | Carrison et al. |
| 2005/0203527 A1 | 9/2005 | Carrison et al. |
| 2005/0234425 A1 | 10/2005 | Miller et al. |
| 2005/0261692 A1 | 11/2005 | Carrison et al. |
| 2006/0004369 A1 | 1/2006 | Patel et al. |
| 2006/0064101 A1 | 3/2006 | Arramon |
| 2006/0110017 A1 | 5/2006 | Tsai et al. |
| 2006/0111728 A1 | 5/2006 | Abdou |
| 2006/0129062 A1 | 6/2006 | Nicoson et al. |
| 2006/0229550 A1 | 10/2006 | Staid et al. |
| 2006/0239982 A1 | 10/2006 | Simpson |
| 2006/0258951 A1 | 11/2006 | Bleich et al. |
| 2006/0259060 A1 | 11/2006 | Whitson et al. |
| 2006/0264994 A1 | 11/2006 | Schomer et al. |
| 2006/0271196 A1 | 11/2006 | Saal et al. |
| 2006/0271197 A1 | 11/2006 | Saal et al. |
| 2006/0284994 A1 | 12/2006 | Kim |
| 2007/0055259 A1 | 3/2007 | Norton et al. |
| 2007/0135768 A1 | 6/2007 | Carlsen |
| 2007/0142842 A1 | 6/2007 | Krueger et al. |
| 2007/0149895 A1 | 6/2007 | McCullough et al. |
| 2007/0162062 A1 | 7/2007 | Norton et al. |
| 2008/0183175 A1 | 7/2008 | Saal et al. |
| 2008/0183192 A1 | 7/2008 | Saal et al. |
| 2008/0188826 A1 | 8/2008 | Saal |
| 2008/0188827 A1 | 8/2008 | Saal |
| 2008/0214955 A1 | 9/2008 | Speeg et al. |
| 2008/0221586 A1 | 9/2008 | Garcia-Bengochea et al. |
| 2008/0221589 A1 | 9/2008 | Balling et al. |
| 2008/0221605 A1 | 9/2008 | Saal et al. |
| 2008/0255563 A1 | 10/2008 | Farr et al. |
| 2008/0294166 A1 | 11/2008 | Goldin et al. |
| 2008/0294167 A1 | 11/2008 | Schumacher et al. |
| 2008/0319341 A1 | 12/2008 | Taylor et al. |
| 2009/0048678 A1 | 2/2009 | Saal et al. |
| 2009/0076486 A1 | 3/2009 | Cucin |
| 2009/0105609 A1 | 4/2009 | Thompson et al. |
| 2009/0216234 A1 | 8/2009 | Farr et al. |
| 2009/0259126 A1 | 10/2009 | Saal et al. |
| 2010/0063416 A1 | 3/2010 | Cicenas et al. |
| 2010/0152611 A1 | 6/2010 | Parihar et al. |
| 2010/0297577 A1 * | 11/2010 | Cohen .................. 433/92 |
| 2011/0054349 A1 | 3/2011 | Hibner |
| 2011/0098596 A1 | 4/2011 | Ozturk et al. |
| 2011/0160731 A1 | 6/2011 | Bleich et al. |
| 2011/0306879 A1 | 12/2011 | Saal et al. |
| 2011/0313433 A1 | 12/2011 | Woodard, Jr. et al. |
| 2012/0004595 A1 | 1/2012 | DuBois et al. |
| 2012/0283742 A1 | 11/2012 | Dubois et al. |
| 2013/0046199 A1 | 2/2013 | DuBois et al. |
| 2013/0172919 A1 | 7/2013 | Carrison |
| 2013/0211321 A1 | 8/2013 | DuBois et al. |
| 2013/0211438 A1 | 8/2013 | DuBois et al. |
| 2013/0218186 A1 | 8/2013 | DuBois et al. |
| 2013/0310834 A1 | 11/2013 | Dubois et al. |

FOREIGN PATENT DOCUMENTS

| | | |
|---|---|---|
| RU | 2029533 | 2/1995 |
| WO | WO 93/14700 | 8/1993 |
| WO | WO 97/26835 | 7/1997 |
| WO | WO 2006/027549 | 3/2006 |
| WO | WO 2006/119455 | 11/2006 |
| WO | WO 2008/094436 | 8/2008 |
| WO | WO 2008/094444 | 8/2008 |
| WO | WO 2008/094439 | 9/2008 |
| WO | WO 2008/095177 | 10/2008 |
| WO | WO 2009/052194 | 4/2009 |
| WO | WO 2009/124192 | 10/2009 |
| WO | WO 2012/003383 | 1/2012 |

* cited by examiner

DEVICES AND METHODS FOR FILTERING AND/OR COLLECTING TISSUE

FIELD OF THE INVENTION

The present devices and methods relate generally to medical devices and methods for filtering and/or collecting tissue, which has been cut or resected from various regions of a patient's body.

BACKGROUND

Many common medical devices perform the function of resecting tissue. Suction, supplied by an external vacuum source is often used to evacuate tissue from the operative site.

Medical devices which cut and evacuate tissue are used in a variety of procedures, including ear, nose, and throat surgery, gynecological surgery, spinal surgery, ophthalmic surgery, and many other applications. Depending on the procedure, the evacuated tissue may be collected for analysis.

It is often desirable to capture tissue for analysis to check for pathogens, cancerous, and precancerous cells.

A fluid medium such as air, water, or a combination of air and water are frequently used to conduct resected tissue away from the operative site where it was resected.

Flow through a tissue collection chamber (alternatively referred to as a filter) may be reduced as tissue is collected in the chamber. This occurs when the tissue obstructs flow through the filter media. The reduction in flow through the filter and consequently through the cutting device may prolong the procedure by reducing the efficiency of the cutting device. Furthermore, the clogged filter may reduce the flow of suction available and result in increased clogging of the cutting device and/or limit the amount of tissue that can be collected or filtered.

As a result of the above limitations, there is a need for an improved filter or tissue collection device that minimizes or eliminates such limitations or restrictions.

BRIEF SUMMARY

Various devices and methods for filtering and/or collecting tissue which has been cut or resected from various regions of a patient's body are described herein.

In certain variations, a filter for filtering and/or collecting tissue resected from a patient may include an inner chamber having a first end, a second end, and a wall. The wall may include one or more openings. The filter may include an outer chamber having a first end, a second end, a wall, an outlet port, an inlet port. An outer chamber lid may also be provided. The outer chamber may be configured to receive the inner chamber. The inner chamber is removably inserted in the outer chamber and the inner chamber is positioned within the outer chamber such that a gap is maintained between an outer surface of the wall of the inner chamber and an inner surface of the wall of the outer chamber. The gap may include a gap first portion and a gap second portion. The width of the gap first portion may be less than a width of the gap second portion. The filter may allow a fluid or fluid medium having resected tissue therein to flow through the inlet port into the inner chamber and at least partially through the openings in the wall of the inner chamber. The filter may remove resected tissue from the fluid medium by allowing the fluid medium to pass through the gap first portion, through the gap second portion and out of the outlet port, while the gap first portion inhibits or prevents the passage of resected tissue through the gap first portion and resected tissue is collected in the inner chamber.

In certain variations, a method of filtering and/or collecting tissue resected from a patient may include one or more of the following steps. A fluid medium having resected tissue therein is passed into a filter. The filter may include an outer chamber having an outlet port, an inlet port, an outer chamber lid, and an inner chamber removably inserted in the outer chamber. The inner chamber may have a first end, a second end, and a wall. The wall may include one or more openings and the inner chamber may be positioned in the outer chamber such that a gap is maintained between an outer surface of the wall of the inner chamber and an inner surface of a wall of the outer chamber. The gap may include a gap first portion and a gap second portion. The fluid medium having resected tissue therein may be passed through the inlet port of the outer chamber, where the fluid medium and resected tissue impact the second end of the inner chamber, which is positioned adjacent to the outlet port of the outer chamber. The fluid medium having resected tissue therein is passed at least partially through the openings in the wall of the inner chamber. Resected tissue is removed from the fluid medium by allowing the fluid medium to pass through the gap first portion, through the gap second portion and then out of the outlet port, while the gap first portion inhibits or prevents the resected tissue from passing through the gap first portion. The resected tissue is collected in the inner chamber thereby filling the inner chamber with tissue from the second end of the inner chamber to the first end of the inner chamber while the fluid medium continues to flow out of the inner chamber and out of the outlet port until the filter is filled or substantially filled with tissue.

DETAILED DESCRIPTION

Figure 1:
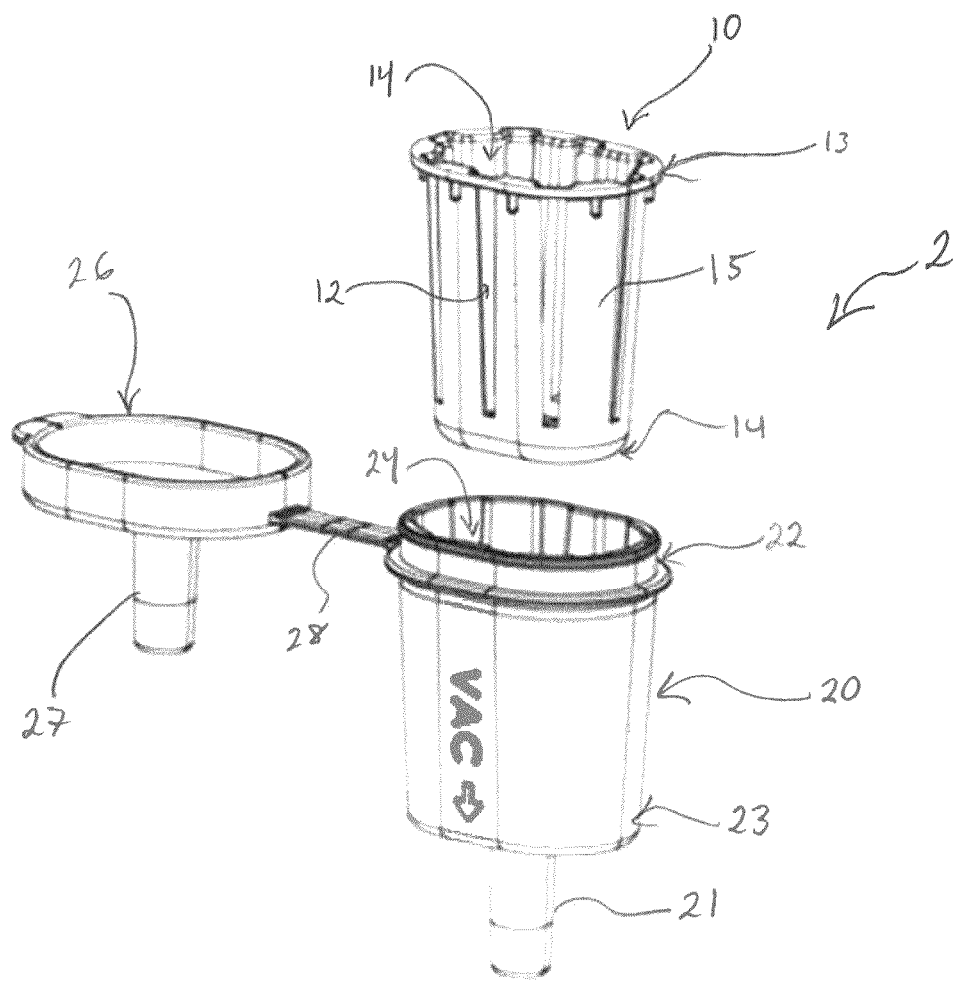
FIG. 1 illustrates a variation of a filter showing the inner chamber suspended over the outer chamber.

Variations of the devices are best understood from the detailed description when read in conjunction with the accompanying drawings. It is emphasized that, according to common practice, the various features of the drawings may not be to-scale. On the contrary, the dimensions of the various features may be arbitrarily expanded or reduced for clarity.

The drawings are taken for illustrative purposes only and are not intended to define or limit the scope of the claims to that which is shown.

In certain variations, a filter or tissue collection chamber for collecting tissue that has been resected, cut or excised from a patient is provided. The filter or tissue collection chamber may include an inner chamber for receiving a fluid medium (e.g., air, water or other fluid or a combination thereof) and resected tissue. The inner chamber includes a first end and a second end. The first end of the inner chamber includes one or more openings through which a fluid medium having resected tissue therein enters the inner chamber. The second end of the inner chamber may be completely or partially closed. For example, in certain variations, the second end of the inner chamber may include one or more or a plurality of openings that allow fluid to pass through the second end of the inner chamber and out of the inner chamber, but the openings may be configured or sized to restrict, prevent or inhibit the passage of tissue through the openings, thereby trapping the resected tissue in the inner chamber.

The inner chamber may include one or more walls extending from the first end to the second end of the inner chamber. The wall may be a single wall or a plurality of walls extending around the circumference of the inner chamber and defining the chamber or receptacle of the inner chamber. The wall may include one or more openings. For example, the openings may be in the form of slots. A slot may extend along a length of the inner chamber wall, for example, extending along the entire length of the inner chamber wall, from the first end of the inner chamber wall to the second end of the inner chamber wall, or along at least a portion of the length of the inner chamber wall. A slot may have a variety of dimensions. For example, the slot may include a width and a length, where the length is greater than the width. In certain variations, the wall of the inner chamber may include a plurality or series of slots positioned around the circumference of the inner chamber. Each slot may be separated from an adjacent slot by at least a portion of the wall, creating an alternating arrangement of slots and walls or wall portions. In certain variations, the walls of the inner chamber may be comprised of a series of slots and walls around the circumference of the inner component. The walls may be separated by multiple openings preferentially extending at least a portion of the height of the inner chamber to form slots.

The filter may include an outer chamber. The outer chamber may include a first end and a second end. The outer chamber may be configured to receive the inner chamber. An end of the outer chamber may include one or more openings for receiving the inner chamber. One end of the outer chamber may include an inlet port through which a fluid medium or fluid medium carrying resected tissue enters the filter. The other end or second end of the outer chamber may include an outlet port through which a fluid medium exits the filter after passing through the filter. In certain variations, the outer chamber may be configured to receive the inner chamber, e.g., an end of the outer chamber may have an opening for receiving the inner chamber, and a lid or other cover, having an outlet port through which a fluid medium exits the filter after passing through the filter, may be positioned over the end and may cover the inner chamber positioned therein. Alternatively, the lid or other cover may have an inlet port through which a fluid medium or fluid medium carrying resected tissue enters the filter.

The outer chamber may include one or more walls extending from the first end to the second of the outer chamber. The wall may be a single wall or a plurality of walls extending around the circumference of the outer chamber and defining the chamber or receptacle of the outer chamber in which the inner chamber may be received or positioned.

The outer chamber may include an outer chamber lid or cap. The outer chamber lid may include an inlet port through which a fluid medium or fluid medium carrying resected tissue enters the filter. Alternatively, the outer chamber lid or cap may include an outlet port through which a fluid medium exits the filter after passing through the filter. The outer chamber lid may be integral to the outer chamber or may be a separate component from the outer chamber. In certain variations, the outer chamber lid may be coupled to the outer chamber. For example, the outer chamber lid may be coupled to the outer chamber wall or body with a linkage or flexible member which acts as a hinge to allow the outer chamber lid to open and close over the opening at the first end of the outer chamber. The lid may close over the outer chamber opening and create or form a seal or closure with the outer chamber, e.g., over a first or second end or lip of the outer chamber, to prevent leakage. The lid may make or may not make contact with the first end of the inner chamber, when the inner chamber is positioned in the outer chamber. Optionally, the lid may make contact with an end of the inner chamber when the inner chamber is positioned in the outer chamber, forming a seal or closure with the inner chamber and the outer chamber to prevent leakage. Optionally, the flexible member may be an integrated flexible member.

The inlet port and outlet port are configured to be connected to a conduit, tubing or other connector through which a fluid medium is conducted. The fluid medium may include resected tissue. For example, a tubing or conduit may be coupled or connected to the inlet port by being positioned over the inlet port. A tubing or conduit may be coupled or connected to the outlet port by being positioned over the outlet port. In other variations, a conduit, tubing or other connector may be coupled or connected to the inlet port and/or the outlet port by being inserted into the inlet port or outlet port or by forming other connections or being configured to accept a piece of tubing or conduit.

A fluid medium with resected tissue may flow into and enter the filter through the inlet port, e.g., flowing from a connected conduit or tubing that conducts the fluid medium and/or resected tissue to flow into the filter, through the inlet port. The fluid medium may include a gas, liquid, or a combination thereof. The filter is designed to collect all or a portion of the resected tissue within the inner chamber before or as the fluid medium flows out of the outlet port.

The inner chamber may be removably inserted or positioned in or within the outer chamber. The inner chamber may be positioned in the outer chamber such that a gap or space is maintained between an outer surface of the wall of the inner chamber and an inner surface of the wall of the outer chamber. The gap may have varying dimensions or a single uniform dimension. For example, the gap may include a gap first portion and a gap second portion. The width of the gap first portion may differ from the width of the gap second portion. The width of the gap first portion may be less than the width of the gap second portion. The gap first portion may have a depth or length that is greater than or equal to its width. The width may refer, e.g., to the distance between the wall of the inner chamber and the wall of the outer chamber. In certain variation, one or more or several gaps or gap portions, e.g., having varying widths or sizes, may be provided between the inner and outer chambers.

A fluid medium carrying resected tissue may flow through an inlet port of the outer chamber or outer chamber lid and flow from the inlet port into the inner chamber. The fluid medium having resected tissue therein may then flow at least partially through the openings or slots in the wall of the inner chamber. The filter removes or separates resected tissue from the fluid medium by allowing the fluid medium to pass through the gap first portion and then through the gap second portion and ultimately out of the outlet port of the outer chamber. However, the gap first portion inhibits or prevents the resected tissue from passing through the gap first portion. The gap first portion has dimensions or a width which is sized to allow the fluid medium to pass through the gap first portion but to inhibit tissue from passing through the gap first portion. In certain variations, the dimensions or width of a gap or gap first portion may vary depending on the particular use of the device, e.g., depending on the type and size of the objects or tissue to be collected or filtered. The tissue that is inhibited from passing through the gap first portion is collected in the inner chamber. The collected tissue may be protruding out of the slots and/or it may be flush with the slots, yet still be held by the inner chamber. The tissue may be behind the slots in the inner chamber as well. The collected tissue remains held by the inner chamber, such that upon removal of the inner chamber from the outer chamber, the tissue can be removed from the filter with the inner chamber, and then emptied out of the inner chamber for testing, disposal or other use.

The gap first portion may have a depth that is greater than its width. The greater depth creates a long passageway making it difficult for any resected tissue that may enter the gap first portion to navigate through the entire length or depth of the gap first portion. If any resected tissue passes through the entire gap first portion, the wider gap second portion allows the piece of resected tissue to pass from the gap second portion to the outlet port and to exit the filter, thereby preventing or reducing tissue clogging in the gap or space or gap second portion between the inner chamber and the outer chamber to avoid, reduce or prevent a reduction in fluid flow rate.

The outer chamber wall may have a varying wall thickness around its circumference or around at least a portion of its circumference to provide varying space between the inner chamber and the outer chamber. For example, this may provide the gap first portion with a width that is less than the width of the gap second portion. In certain variations, the inner chamber wall may have a varying wall thickness. In certain variations, the varying wall thicknesses of the inner and/or outer chamber walls may create one or more gaps or spaces of varying size or width between the chambers.

The varying space or gap between the inner chamber and outer chamber may inhibit or prevent the passage of objects larger than the gap or space while allowing the fluid medium to pass through the smaller gaps or spaces and then to flow freely through the larger gaps or spaces. This provides a path for the fluid to flow through a slot or opening in the inner chamber, through the narrow space (e.g., the gap first portion) between the walls of the inner chamber and outer chamber, and into the wider space (e.g., the gap second portion which may be wider than the gap first portion) between the inner chamber and outer chamber. The spacing between the surfaces of the inner chamber or component and the outer chamber or component may be adequate to allow a fluid medium to pass but restricts or inhibits the flow of tissue thereby collecting the tissue in the tissue collection chamber.

In certain variations, the gap may have a constant width, such that there is no varying width between the gap first portion and the gap second portion, e.g., the gap first portion may have a width that is equal to the width of the gap second portion. In certain variations, there may be a single gap having a constant width around the entire circumference of the filter.

In certain variations, a gap may have a width that is less than, equal to or greater than its length or depth.

In certain variations, the inner chamber may be positioned into the outer chamber such that the wall of the outer chamber is spaced away from the wall of the inner chamber in a controlled manner to maintain consistent spacing between the inner chamber and the outer chamber. The space or gap between the walls of the inner and outer chambers may be sized not to allow tissue larger than the size or width of the space or gap (i.e., the distance between the outer surface of the wall of the inner chamber and the inner surface of the wall of the outer chamber) to pass into the outer chamber or out of the outlet port. For example, if the spacing or width between the walls of the inner chamber and outer chamber is 0.020 of an inch, then objects, such as tissue, that are larger than 0.020 of an inch will not pass through the spacing and such objects will be restricted or inhibited and collected in the inner chamber. In certain variations, the gap first portion may be about 0.020 of an inch in width and the gap second portion may be larger than 0.020 of an inch in width.

The filter may include one or more components or features configured to position the inner chamber within the outer chamber such that a consistent spacing is maintained between the outer surface of the inner chamber wall and the inner surface of the outer chamber wall. For example, the outer chamber or the inner chamber may include one or more components or features to properly position the inner chamber within the outer chamber such that a consistent and stable spacing is provided and maintained between the outer surface of the inner chamber wall and the inner surface of the outer chamber wall.

The various filter designs described herein can filter tissue while minimizing flow losses as the tissue is collected. The filters may also provide easy access to collected tissue, where the inner chamber may be removed in order to empty or sample the tissue collected therein, while the filter and outer chamber remains connected or coupled to a tissue cutting device. Removal of tissue may be assisted by slots which or long or vertically arranged and/or sloped, where tissue slides down the slots and out of the inner chamber end opening during emptying without being held up or restricted by the slots. The various filter designs described herein may have rigid or non-rigid components which are completely or at least partially rigid or non-rigid. For example, the outer chamber may be rigid, where the inner chamber is non-rigid allowing for some flexibility as it is inserted or removed from the outer chamber. In certain variations, the inner and outer chamber may both be rigid, both be non-rigid, one can be rigid while the other is non-rigid, and/or the outer chamber lid may be non-rigid or rigid. In certain variations, the components of the filter may be transparent or opaque or a combination thereof.

The various filters or tissue collection devices described herein may be used with a variety of medical instruments, including, e.g., various tissue cutting or resection devices or various aspirators, to assist with the collection of tissue removed or resected from various anatomical regions of a patient. The tissue cutting or resection devices may utilize vacuum suction for tissue removal and/or may be powered by a variety of power sources, including, e.g., vacuum power, electrical power, battery power, gas power, compressed or pressurized gas power. For example, in certain variations, the various filters or tissue collection devises described herein may be used with any of the medical instruments described in US Pub. App. 2013/0211438; US Pub. App. 2013/0046199; or US Pub. App. 2013/0218186.

In use, in certain variations and with certain tools or instruments, the filter may be positioned on its side or in a horizontal position or orientation. For example, the tissue and fluid medium may enter the filter and the tissue may fill the inner chamber of the filter from one end, e.g., a second end, adjacent the outlet port of the outer chamber, to the other end, e.g., a first end, adjacent the inlet port of the outer chamber, regardless of the orientation of the filter. For example, the suction pulled through the device may cause the fluid medium and/or resected tissue to enter the filter and impact the second end of the inner chamber first, filling the inner chamber from a second end of the inner chamber to the first end of the inner chamber. The filter may be used in any orientation, e.g., horizontal or vertical relative to the patient or the instrument used to resect, cut or remove tissue or other material FIG. 1 illustrates one variation of a filter 2 or tissue collection chamber. The filter 2 includes an inner chamber 10. The inner chamber has a first end 13 and a second end 14. The filter 2 includes an outer chamber 20. The outer chamber 20 has a first end 22 and a second end 23. The outer chamber includes an outlet port 21. The outer chamber 20 may include an outer chamber lid 26, which is coupled to the outer chamber 20 and may be opened and closed. The outer chamber lid includes an inlet port 27 for receiving a fluid medium and/or resected tissue. The inner chamber 10 can be inserted into the outer chamber 20 by opening or removing the outer chamber lid 26, and inserting the inner chamber 10 into the opening 24 of the outer chamber 20. In FIG. 1, the inner chamber 10 is shown outside of the outer chamber 20. Alternatively, in certain variations, the outer chamber lid can include an outlet port and may be configured to cover the end of the outer chamber opposite an end having an inlet port.

The wall 15 or plurality of walls of the inner chamber 10 may include one or more slots 12 or openings. These slots 12 or openings allow fluid and/or tissue to pass therethrough. The outer chamber lid 26 includes an opening or inlet port 27 to allow fluid and/or objects, such as tissue, to enter the inner chamber 10 of the filter 2 or tissue collection chamber. The outer chamber 20 may also include an outlet port 21 or opening on a bottom or at or near the second end 23 of the outer chamber 20 to allow fluid and tissue or other objects too small to be trapped within the inner chamber 10 to exit the filter or tissue collection device. The outer chamber 20 may include an integrated flexible member 28 which acts as a hinge to allow the lid 26 to open and/or close over the opening 24 of the outer chamber 20 and/or over the inner chamber 10 positioned within the outer chamber 20, to form a seal with the first end 22 of the outer chamber 20 to prevent leakage. In certain variations, the lid 26 may form a seal with at least a portion of the first end 22 of the outer chamber and/or at least a portion of the first end 13 of the inner chamber 10.

Figure 2:
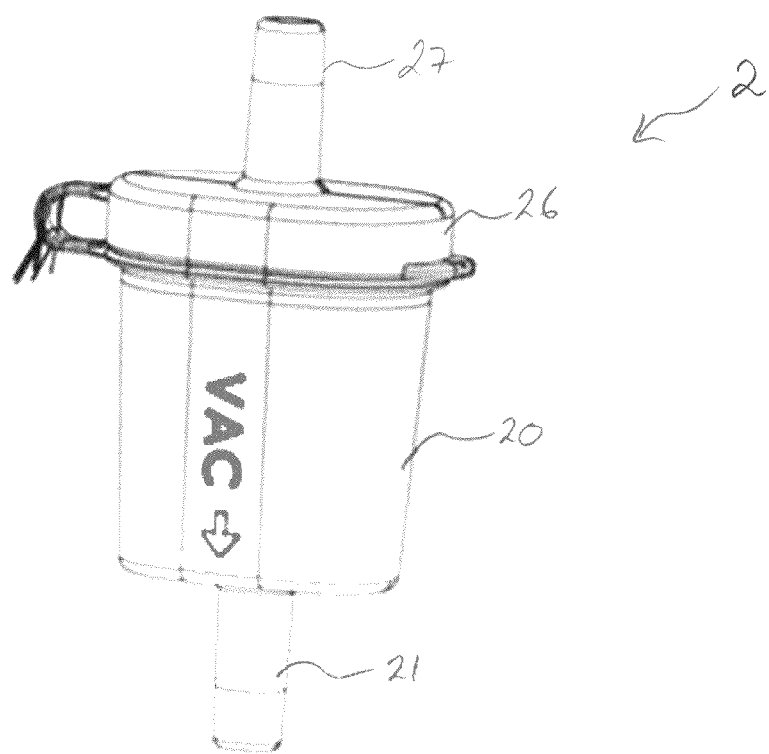
FIG. 2 illustrates a variation of a filter where the lid of the outer chamber is in a closed position over the opening of the outer chamber.

As illustrated in FIG. 2, once the inner chamber 10 is positioned in the outer chamber 20, the outer chamber lid 26 may be closed down over the opening 24 of the outer chamber and/or over the inner chamber 10 positioned in the opening 24. The outer lid 26 may be closed around at least a portion of the first end 22 of the outer chamber 20 providing a fluid tight seal to prevent leakage of fluid, tissue and/or vacuum.

Figure 3A:
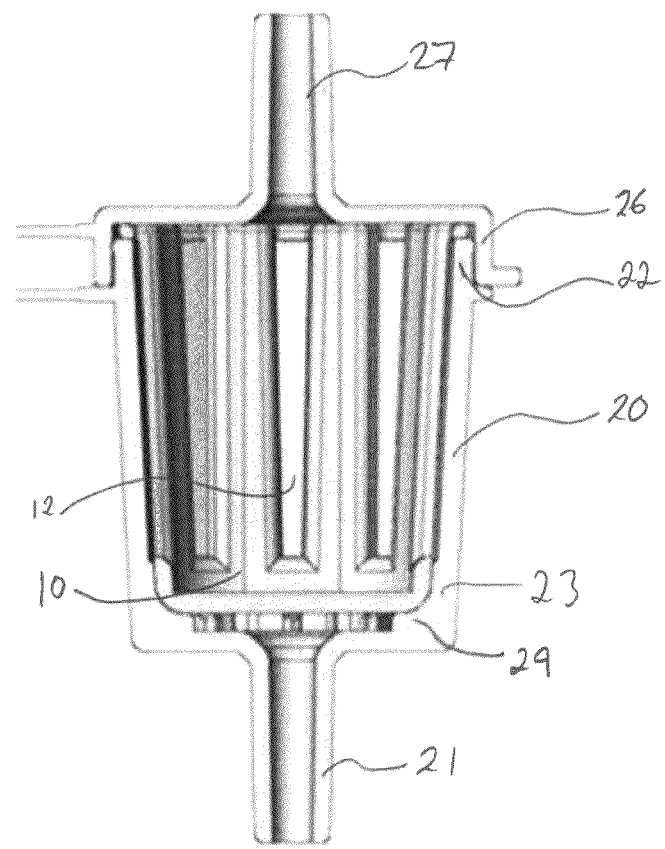
FIG. 3A illustrates a cross sectional view along a vertical plane of the filter of FIG. 2, where the inner chamber is positioned within the outer chamber and the lid of the outer chamber is in a closed position.

FIG. 3A illustrates a cross sectional view along a vertical plane of the filter 2 where the inner chamber 10 is positioned within the outer chamber 20 and the lid 26 of the outer chamber 20 is in a closed position. The inlet port 27 or entrance port is located on the outer chamber lid 26, at the top or first end of filter 2. The inlet port 27 allows fluid and/or objects such as tissue to flow into the filter 2, and into the inner chamber 10. The outlet port 21 or exit port is located at the second end 23 of the outer chamber or at the bottom of the device. The outlet port 21 allows fluid and/or objects that are not collected or trapped in the inner chamber 10 of the filter or tissue collection chamber to flow out of the filter. The slots 12 through the walls of the inner chamber 10 are visible in FIG. 3. The inner chamber 10 includes an array of slots 12 around the circumference of the inner chamber.

In certain variations of the filter 2, support or alignment features or components 29 may be located on the inside of the outer chamber 20, e.g., at one or more inner corners of the outer chamber 20 or other location on the outer chamber 20. The support or alignment features or components 29 keep the inner chamber 10 properly positioned relative to the outer chamber 20 thereby maintaining proper or consistent spacing between the inner chamber 10 and the outer chamber 20. For example, the inner chamber 10 may sit or rest on or be received within the support components or features 29 such that a gap or space of a uniform or varying width (e.g., a gap having different gap portions with different widths or one or more gaps with different widths) is maintained consistently between the inner chamber 10 and the outer chamber 20, e.g., around the entire circumference of the filter.

Figure 3B:
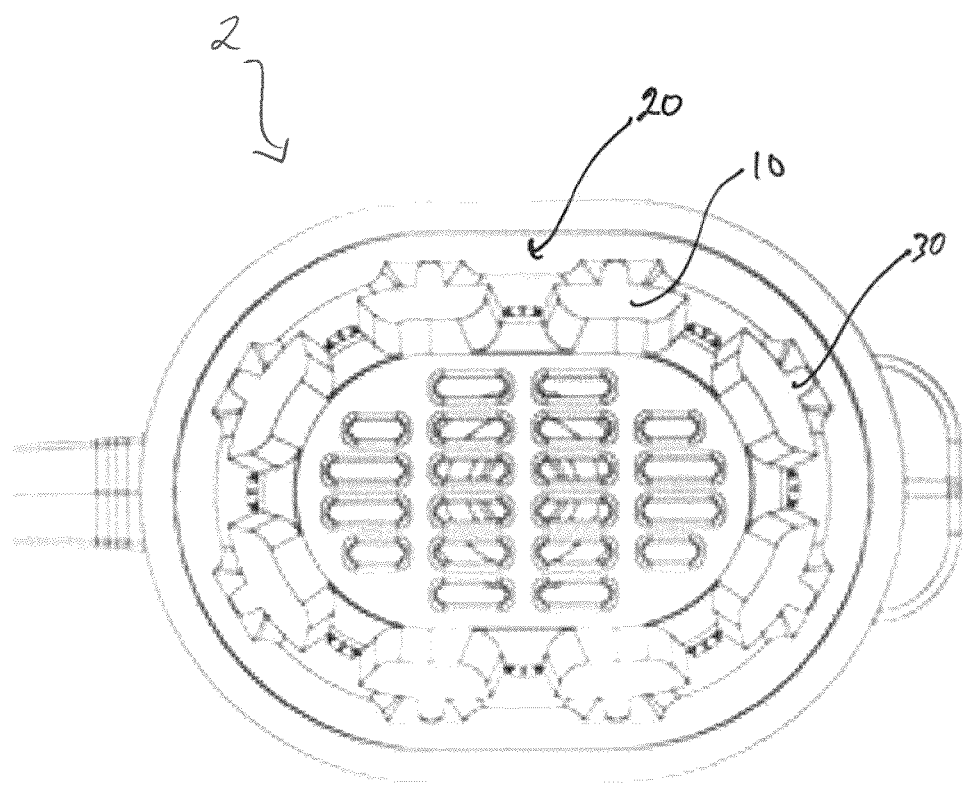
FIG. 3B illustrates a cross sectional view through a horizontal plane of the filter of FIG. 2, looking toward the outlet port fluid exit of the outer chamber.

Optionally, as shown in FIG. 3B, which shows a cross sectional view through a horizontal plane of the filter 2, the inner chamber 10 may include support or alignment features or components 30, e.g., positioned at the first end of the inner chamber 10, on the outside surface of inner chamber wall or anywhere on the inner chamber. These support or alignment features or components may separate the inner chamber 10 from the outer chamber 20, helping to maintain a consistent gap or spacing between the inner chamber and the outer chamber 20. In certain variations, the outer chamber and/or the inner chamber may include support features or components.

Figure 4:
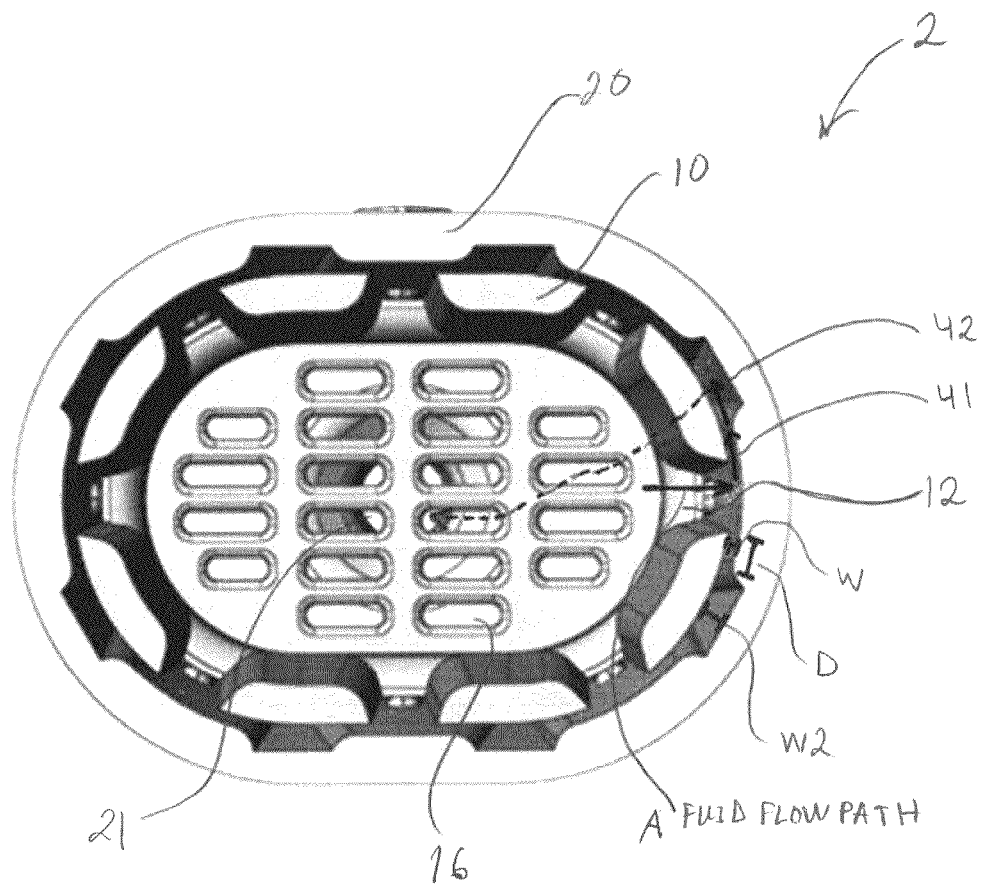
FIG. 4 illustrates a cross sectional view through a horizontal plane of the filter of FIG. 2, looking toward the outlet port fluid exit of the outer chamber, including arrows depicting the fluid flow path through the filter.

FIG. 4 illustrates a cross sectional view through a horizontal plane of the filter 2, looking toward the outlet port 21 or exit port of the outer chamber 20. The inner chamber 10 is positioned within the outer chamber 20. The inner chamber 10 includes a plurality of openings 16 at the second end 14 of the inner chamber 10. These openings 16 may allow the passage of fluid, while restricting or inhibiting the passage of tissue or objects that are larger than the openings 16. Optionally, the inner chamber 10 may have no openings at the second end 14, which may be completely solid.

The inner chamber 10 is positioned within the outer chamber 20 such that a gap or space is maintained between the wall of the inner chamber 10 and the wall of the outer chamber 20. The gap may include a gap first portion 41 and a gap second portion 42. The gap first portion 41 may have a width W that is smaller than its depth D. The gap first portion 41 may have a width W that is smaller than the width W2 of the gap second portion 42. The gap first portion 41 is in fluid communication with and leads into the gap second portion 42. The gap second portion 42 is in fluid communication with and leads to the outlet port 21 of the outer chamber 20 to allow fluid to that passes through the filter, to exit the filter. Some objects or tissue not trapped or restricted by the gap first portion 41 may pass through the wider gap second portion 42 and out of the outlet port 21.

In FIG. 4, the variable wall thickness of the outer chamber 20 is visible showing the gaps or spaces between the inner chamber and outer chamber walls. The variable wall thickness in the outer chamber wall helps create the gap first portion 41 and the gap second portion 42, where the gap first portion 41 has a width W that is smaller than the width W2 of the gap second portion 42. The fluid medium would flow generally through the slots 12 in the inner chamber through the smaller space or gap first portion 41, between the inner chamber and outer chamber, and into and through the larger space or gap second portion 41, between the inner chamber and outer chamber, and then down to the outlet port 21 and out of the outlet port 21.

FIG. 4 illustrates with arrows A the fluid flow path from the inner chamber, through the gaps (41 and 42) and out of the outlet port 21 (dashed arrow showing a transparent view of flow between inner chamber and outer chamber as it travels to the outlet port). The fluid and/or tissue enters the inner chamber 10 via the inlet port 27 and passes through the slots 12 of the inner chamber. From the slots 12 the fluid then enters into the gap first portion 41. Objects and tissue larger than the gap first portion or a width of the gap first portion are blocked, stopped or inhibited by the gap first portion from passing through the gap first portion 41, filtering the tissue or objects and removing them from the fluid or fluid medium. The fluid passes through the gap first portion 41 and then passes through the gap second portion 42. The fluid then flows from the gap second portion 42 to the outlet port 21 and out of the filter 2 into a tube or other conduit coupled to the filter 2, where the fluid is conducted or taken away from the filter 2.

In certain variations, the fluid medium and/or resected tissue may flow through the inlet port 27 and into the inner chamber 10 to the second end 14 of the inner chamber 10. The fluid medium and tissue then flows through the slots 12. The fluid continues to flow horizontally or laterally (relative to the longitudinal axis of the filter extending from the inlet port to the outlet port) through the gap first portion 41 and through the gap second portion 42, where it then travels down or vertically through the gap second portion, to the outlet port 21, and out of the filter 2, as tissue continues to fill the inner chamber 10 from the second end 14 to the first end 13 of the inner chamber 10, collecting within the inner chamber. The filter 2 minimizes or prevents a reduction in flow or flow rate as tissue is collected and facilitates recovery of collected tissue.

Figure 5A:
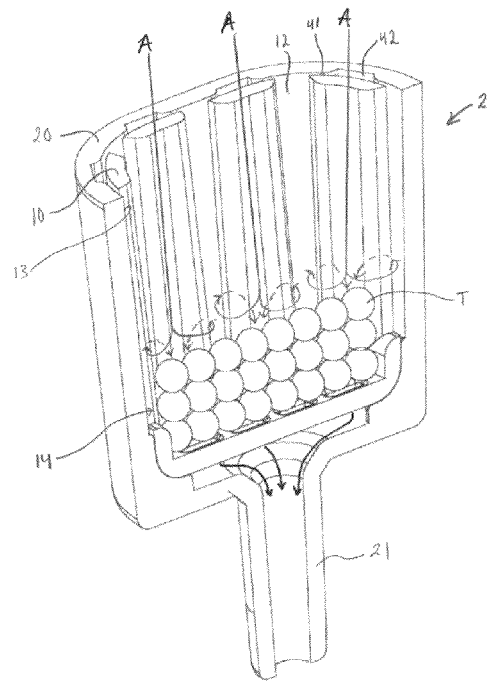
FIGS. 5A-5C illustrate cross sectional views of a variation of a filter at different stages of tissue collection while maintaining fluid flow through the filter.
Figure 5B:
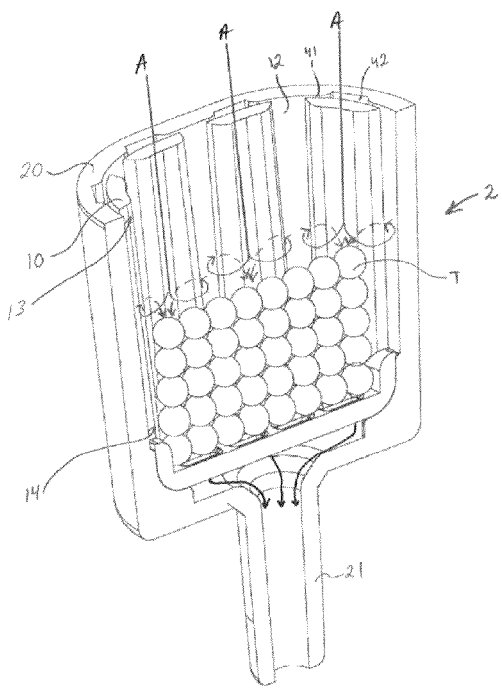
Figure 5C:
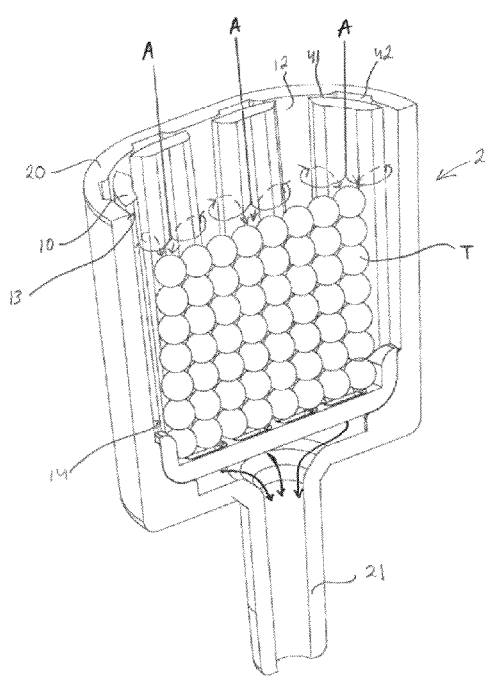

FIGS. 5A-5C illustrate the cross sectional views of a variation of a filter 2 at different stages of tissue collection. Arrows A (with dashed lines representing a transparent view of fluid flow between the inner and outer chambers) show the fluid flow path from the inner chamber, through the gap first portion 41 and gap second portion 42 between the inner chamber 10 and outer chamber 20 and out of the outlet port 21, as tissue T (which is represented generally by the spheres T in the drawings) is collected in the inner chamber 10. The fluid medium carrying resected tissue enters the inner chamber 10 through the inlet port 27, and impacts the second end 14 of the inner chamber 10. The fluid medium with resected tissue then flows through or into the slots 12 and to the gap first portion 41. Once the fluid medium with resected tissue arrives at the gap first portion 41, the fluid continues to flow into the gap first portion 41. However, objects and tissue larger than the gap first portion 41 are stopped or inhibited from passing through the gap first portion 41 (i.e., they are inhibited or blocked by the size or width restrictions of the first gap portion or space between the outer surface of the wall of the inner chamber 10 and the inner surface of the wall of the outer chamber 20). The fluid flows or passes through the gap first portion 41 and then passes through the gap second portion 42. The fluid then flows from the gap second portion 42 to the outlet port 21 and out of the filter 2 into a tube or other conduit coupled to the filter 2, where the fluid is conducted or taken away from the filter 2. As the inner chamber fills with collected tissue, e.g., from the second end 14 or bottom of the inner chamber to the first end 13 or top of the inner chamber, a fluid flow path is maintained through the slots 12, through the gap first portion 41, through the gap second portion 42 and out of the outlet port 21. As a result, the filter can filter and collect tissue while minimizing or substantially reducing any restriction or reduction in flow or flow rate as the inner chamber or filter fills with tissue. For example, the fluid flow rate through the filter may maintain constant or substantially constant as the tissue fills the inner chamber, or it may drop initially, when for example openings at the second end of the inner chamber (in variations having such openings) are blocked with tissue, and then remain constant until the inner chamber is completely or substantially filled or the one or more slots are fully, completely or substantially blocked.

In certain variations of the devices or filters described herein, a width of the gap first portion may be consistent around the entire circumference of the filter and a width of the gap second portion may be consistent around the entire circumference of the filter.

In certain variations, medical devices, including various tissue collection devices or filters and methods for collecting and filtering tissue are provided. In certain variations a tissue collection device may include one or more spaces between an inner chamber wall and an outer chamber wall of the device, which inhibit the passage of tissue while allowing the passage of fluid. The spacing between the inner chamber wall and outer chamber wall may be varied to provide a short path for the fluid to travel through a narrow passageway and then into a larger, less restrictive volume. The fluid medium generally flows through or between slots in the inner chamber, through a small or narrow space between the inner chamber and outer chamber and into a large, less restrictive space between the inner chamber and the outer chamber before then flowing to the exit port and out of the device or filter. Filter of the tissue or removal of the tissue from the fluid medium is performed by the one or more spaces or gaps between two components, i.e., the spaces or gaps between the inner chamber and the outer chamber of the device or filter.

In certain variations, a medical device for collecting tissue includes an inner chamber and an outer chamber wherein fluid medium is capable of passing through narrow passageways between the walls of the inner chamber and the outer chamber while inhibiting the passage of tissue through said passageways. The space between the inner chamber and outer chamber wall may vary in size. The surface of the inner chamber adjacent to the exit port on the outer chamber has openings of an appropriate size to inhibit the passage of objects through the openings while allowing fluid to pass through the openings. The inner chamber may be removed from the outer chamber. The collected objects or tissue may be removed from the medical device and remain in the inner chamber when the inner chamber is removed from the outer chamber. The space between the inner chamber and outer chamber may be controlled by features on the inner chamber. The space between the inner chamber and outer chamber may be controlled by features on the outer chamber. The various filters and tissue collection devices described herein allow for the tissue that is collected within the inner chamber to be easily accessed and facilitate recovery of collected tissue both intra-operatively and post-operatively. The filters described herein facilitate pathological analysis and may allow for the removal of tissue intra-operatively, e.g., to keep tissue from different locations within or on the body isolated from one another.

Methods of filtering and/or collecting tissue resected from a patient may include one or more of the following steps.

A fluid medium having resected tissue therein may be passed into a filter. The filter may include an outer chamber having an outlet port and an outer chamber lid having an inlet port, and an inner chamber removably inserted in the outer chamber. In certain variations, the inlet and outlet ports may be reversed, with the outlet port being on the lid and the inlet port being at another end of the outer chamber. The inner chamber may include a first end, a second end, and a wall extending from the first end to the second end. The wall may include one or more openings and the inner chamber may be positioned in the outer chamber such that a gap is maintained between an outer surface of the wall of the inner chamber and an inner surface of a wall of the outer chamber. The gap may include a gap first portion and a gap second portion.

The fluid medium having resected tissue therein is passed through the inlet port of the outer chamber or outer chamber lid. The fluid medium and resected tissue enter the inner chamber and impact the second end of the inner chamber, which is positioned adjacent to the outlet port of the outer chamber. The fluid medium having resected tissue therein is at least partially passed through the openings in the wall of the inner chamber. The resected tissue is removed or separated from the fluid medium by allowing the fluid medium to pass through the gap first portion, through the gap second portion and then out of the outlet port, while the gap first portion inhibits, blocks or prevents resected tissue from passing through the gap first portion. The resected tissue is collected in the inner chamber by filling the inner chamber with tissue from the second end of the inner chamber (e.g., the end opposite the inlet port) to the first end of the inner chamber (e.g., the end adjacent the inlet port) while the fluid medium continues to flow out of the inner chamber and out of the outlet port, e.g., until the inner chamber is full or substantially full with tissue.

The gap first portion may have a width which is sized to allow the fluid medium to pass through the gap first portion and to inhibit tissue having a size greater than the gap first portion or greater than the width of the gap first portion from passing through the gap first portion. The tissue that is inhibited from passing through the gap first portion may be collected in the inner chamber. The filter may remove resected tissue from the fluid medium by allowing the fluid medium to pass through the gap first portion, from the gap first portion through the gap second portion, and from the gap second portion out of the outlet port. The gap first portion may inhibit or restrict resected tissue from passing through the gap first portion. The outer chamber wall may have a varying thickness around its circumference to provide the gap first portion with a width that is less than the width of the gap second portion. The second end of the inner chamber which is positioned adjacent the outlet port of the outer chamber may include a plurality of openings that allow fluid to pass through the openings, while inhibiting the passage of tissue, thereby trapping tissue in the inner chamber. A consistent spacing may be maintained between the outer surface of the inner chamber wall and the inner surface of the outer chamber wall. The outer chamber may include one or more components configured to position the inner chamber within the outer chamber such that a consistent spacing is maintained between the outer surface of the inner chamber wall and the inner surface of the outer chamber wall. The one or more openings in the wall of the inner chamber may be in the form of a slot, where the slot extends from a first end of the inner chamber wall to the second end of the inner chamber wall. The one or more openings in the wall of the inner chamber may have a width and a length, where the length is greater than the width. The wall of the inner chamber may include a plurality of slots positioned around the circumference of the inner chamber, wherein each slot is separated from an adjacent slot by at least a portion of the wall. The inlet port and outlet port of the filter may be configured for connection to a first tubing and second tubing through which the fluid medium is conducted. The tubing may be coupled to the filter by being positioned over or inserted in the inlet port or the outlet port.

In certain variations, fluid medium and/or tissue flows through the inlet port and into the inner chamber of a filter or tissue collection device. The fluid medium and/or tissue starts filling the inner chamber and slots from a second end of the inner chamber, that is adjacent to the outlet port of the outer chamber, toward a first end of the inner chamber, that is adjacent to the inlet port of the outer chamber. The fluid medium and/or tissue flows through the slots of the inner chamber. The fluid medium flows into the gap first portion, while tissue larger than the width of the gap first portion is inhibited and trapped in the inner chamber. Fluid flows from the gap first portion into the gap second portion, which has a greater width than the gap first portion. The gap second portion leads to the outlet port so that the fluid flows from the gap second portion to the outlet port and fluid flows out of outlet port, thereby exiting the filter. In certain variations, one or more gaps or gap portions having varying sizes or widths may be provided, e.g., a series of successive gaps having varying sizes, widths or dimensions may be provided to inhibit or prevent the passage of tissue between the inner and outer chambers and/or out of the filter.

In the various filter or tissue collection devices described herein, filtration may be performed by the gap or space maintained between two components, i.e., between the inner chamber and an outer chamber of the filter, in contrast to filtering solely through small molded holes or slots in a single component. In the embodiments described herein where the inner chamber has one or more openings in its second end in addition to the openings or slots in the wall of the inner chamber, some filtration may take place via the openings in the second end of the inner chamber as well.

The gap first portion may be longer or deeper than it is wide, such that the fluid medium has to go through a long passageway or hallway rather than a short orifice. A long passageway or hallway configuration of a gap makes it more difficult for tissue that does pass into the gap first portion, e.g., smaller tissue, to navigate or pass through the full length of the gap first portion. If the tissue does get through the gap first portion, it would then enter the gap second portion which is wider than the gap first portion, and allows the tissue to more easily pass through to the outlet port and to exit the filter to prevent clogging of the gaps and the filter by any tissue that inadvertently slips or passes through the gap first portion. One or more gaps may provide a tortuous pathway to inhibit or prevent the passage of tissue out of the filter.

The inner chamber may have one or more slots in the wall of the inner chamber, and the slots may be in fluid communication with the gap. The fluid medium and/or tissue enters the inner chamber and as the slots get loaded with tissue at the second end of the inner chamber, which sits adjacent the outlet port, the first end of the slot (or unfilled or unblocked portion of the slot) still has a fluid flow pathway to allow fluid to pass into the gap while tissue is being collected. Therefore, tissue is filtered from the second end of the inner chamber to the first end of the inner chamber and as a result, the gap doesn't get completely blocked until the filter is nearly full or full, thereby minimizing or eliminating any reduction in flow rate as tissue is collected and starts to block or fill the slots. The filter is not loaded or completely blocked until it is full or nearly full with tissue.

The filter or tissue collection chambers described herein are intended to cause air or other fluid to flow into the inner chamber and through the gap, i.e., through the gap first portion and then into the gap second portion between the inner and outer chambers, and then out of the exit port. This airflow or fluid flow minimizes the restriction to flow while the filter fills with tissue. Additionally, tissue momentum causes the tissue to impact the second end of the filter (adjacent the outlet port) and to stay there rather than flow to the first end of the inner chamber (adjacent the inlet port). As a result, the filter chamber is filled from the second end (outlet port end) to the first end (inlet port end) regardless of the orientation of the filter.

Some of the advantages of the various filters and tissue collection chambers described herein include, among others: The filter is less likely to slow down as tissue is collected and the filter starts to get loaded with tissue. The tissue can easily be removed intra-operatively by removing the inner chamber from the outer chamber and emptying the tissue contents. The filter is easy to manufacture because small filtration features don't have to be created in the plastic tooling.

The above arrangements, materials, and dimensions for the vacuum powered mechanisms described herein are exemplary and are not intended to be limiting.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A filter for collecting tissue resected from a patient comprising:
    an inner chamber having a first end, a second end, and a wall positioned therebetween, wherein the wall comprises one or more slots, wherein each slot provides an elongated opening extending from a first end to a second end of the wall, wherein the inner chamber is configured to collect resected tissue therein and wherein the slots are sloped at an angle relative to a longitudinal axis of the inner chamber to facilitate removal of the collected tissue;
    an outer chamber having a first end, a second end, a wall positioned therebetween, an outlet port an inlet port, and an outer chamber lid, wherein the outer chamber is configured to receive the inner chamber; and
    wherein the inner chamber is removably inserted in the outer chamber and the inner chamber is positioned within the outer chamber such that a gap is maintained between an outer surface of the wall of the inner chamber and an inner surface of the wall of the outer chamber;
    wherein the gap comprises a gap first portion and a gap second portion, wherein a width of the gap first portion is less than a width of the gap second portion; and
    wherein the filter is configured to allow a fluid medium having resected tissue therein to flow through the inlet port into the inner chamber and at least partially through the slots in the wall of the inner chamber, wherein the filter removes resected tissue from the fluid medium by allowing the fluid medium to pass through the gap first portion, through the gap second portion and out of the outlet port, while the gap first portion inhibits the passage of resected tissue through the gap first portion.

2. The filter according to claim 1, wherein the gap first portion has a depth that is greater than its width.

3. The filter according to claim 1, wherein the gap first portion has a width which is sized to allow the fluid medium to pass through the gap first portion and to inhibit the passage of tissue through the gap first portion.

4. The filter according to claim 1, wherein the filter removes resected tissue from the fluid medium by allowing the fluid medium to pass first through the gap first portion, wherein the gap first portion has a width of about 0.020 of an inch, then from the gap first portion through the gap second portion, wherein the gap second portion has a width that is greater than the width of the gap first portion, and then from the gap second portion out of the outlet port, and wherein the gap first portion is sized to inhibit the passage of resected tissue through the gap first portion.

5. The filter according to claim 1, wherein the outer chamber wall has a varying thickness around its circumference to provide the gap first portion with a width that is less than the width of the gap second portion.

6. The filter according to claim 1, wherein the second end of the inner chamber includes a plurality of openings that allow fluid to pass therethrough while inhibiting the passage of tissue, thereby trapping tissue in the inner chamber.

7. The filter according to claim 1, further comprising one or more components configured to hold or position the inner chamber within the outer chamber such that a gap or spacing is maintained between the outer surface of the inner chamber wall and the inner surface of the outer chamber wall around the entire circumference of the filter.

8. The filter according to claim 7, wherein the outer chamber comprises the one or more components configured to hold or position the inner chamber within the outer chamber such that a gap or spacing is maintained between the outer surface of the inner chamber wall and the inner surface of the outer chamber wall around the entire circumference of the filter.

9. The filter according to claim 1, wherein a width of the gap first portion is consistent around the entire circumference of the filter and a width of the gap second portion is consistent around the entire circumference of the filter.

10. The filter according to claim 1, wherein the one or more slots in the wall of the inner chamber have a width and a length, wherein the length is greater than the width.

11. The filter according to claim 1, wherein the wall of the inner chamber comprises a plurality of slots positioned around the circumference of the inner chamber, wherein each slot is separated from an adjacent slot by at least a portion of the wall.

12. The filter according to claim 1, wherein the outer chamber lid is coupled to the outer chamber by a linkage or hinge.

13. The filter according to claim 1, wherein the inlet port and outlet port are configured for connection to a first tubing and second tubing through which the fluid medium is conducted, wherein the tubing is coupled to the filter by being positioned over the inlet port or the outlet port.

14. A method of filtering and collecting tissue resected from a patient comprising:
passing a fluid medium having resected tissue therein into a filter, wherein the filter comprises an outer chamber having an outlet port, an inlet port, an outer chamber lid, and an inner chamber removably inserted in the outer chamber, the inner chamber having a first end, a second end, and a wall positioned therebetween, wherein the wall comprises one or more slots wherein each slot provides an elongated opening extending from a first end to a second end of the wall, wherein the inner chamber is configured to collect resected tissue therein and wherein the slots are sloped at an angle relative to a longitudinal axis of the inner chamber to facilitate removal of the collected tissue, and wherein the inner chamber is positioned in the outer chamber such that a gap is maintained between an outer surface of the wall of the inner chamber and an inner surface of a wall of the outer chamber, wherein the gap comprises a gap first portion and a gap second portion;
passing the fluid medium having resected tissue therein through the inlet port of the outer chamber, wherein the fluid medium and resected tissue impact the second end of the inner chamber, which is positioned adjacent to the outlet port of the outer chamber;
passing the fluid medium having resected tissue therein at least partially through the slots in the wall of the inner chamber;
removing resected tissue from the fluid medium by allowing the fluid medium to pass through the gap first portion, through the gap second portion and then out of the outlet port, while the gap first portion inhibits the resected tissue from passing through the gap first portion; and
wherein the resected tissue is collected in the inner chamber thereby filling the inner chamber with tissue from the second end of the inner chamber to the first end of the inner chamber while the fluid medium continues to flow out of the inner chamber and out of the outlet port.

15. The method according to claim 14, wherein the gap first portion has a width which is sized to allow the fluid medium to pass through the gap first portion and to inhibit tissue from passing through the gap first portion.

16. The method according to claim 14, further comprising collecting the tissue that is inhibited from passing through the gap first portion in the inner chamber.

17. The method according to claim 14, wherein the filter removes resected tissue from the fluid medium by allowing the fluid medium to pass through the gap first portion, wherein the gap first portion has a width of about 0.020 of an inch, from the gap first portion through the gap second portion, wherein the gap second portion has a width that is greater than the width of the gap first portion, and from the gap second portion out of the outlet port, and wherein the gap first portion is sized to inhibit resected tissue from passing through the gap first portion.

18. The method according to claim 14, wherein the outer chamber wall has a varying thickness around its circumference to provide the gap first portion with a width that is less than the width of the gap second portion.

19. The method according to claim 14, wherein the second end of the inner chamber includes a plurality of openings that allow fluid to pass therethrough while inhibiting the passage of tissue, thereby trapping tissue in the inner chamber.

20. The method according to claim 14, further comprising maintaining a spacing between the outer surface of the inner chamber wall and the inner surface of the outer chamber wall around the entire circumference of the filter.

21. The method according to claim 20, wherein the outer chamber comprises one or more components configured to position the inner chamber within the outer chamber such that a spacing is maintained between the outer surface of the inner chamber wall and the inner surface of the outer chamber wall around the entire circumference of the filter.

22. The method according to claim 14, wherein the one or more slots in the wall of the inner chamber have a width and a length, wherein the length is greater than the width.

23. The method according to claim 14, wherein the wall of the inner chamber comprises a plurality of slots positioned around the circumference of the inner chamber, wherein each slot is separated from an adjacent slot by at least a portion of the wall.

24. The method according to claim 14, wherein the inlet port and outlet port are configured for connection to a first tubing and second tubing through which the fluid medium is conducted, wherein the tubing is coupled to the filter by being positioned over the inlet port or the outlet port.

25. The method according to claim 14, wherein a width of the gap first portion is consistent around the entire circumference of the filter and a width of the gap second portion is consistent around the entire circumference of the filter.

* * * * *